US 6,599,240 B2

(12) United States Patent
Puchovsky et al.

(10) Patent No.: US 6,599,240 B2
(45) Date of Patent: Jul. 29, 2003

(54) SEGMENTED ARM ASSEMBLY FOR USE WITH A SURGICAL RETRACTOR AND INSTRUMENTS AND METHODS RELATED THERETO

(75) Inventors: Sylvia Puchovsky, Quincy, MA (US); Matthew L. Parsons, Taunton, MA (US); Scott Hunt, Franklin, MA (US); Martin J. Weinstein, South Dartmouth, MA (US); Thomas E. Martin, Riverside, RI (US); Thomas Motta, Assonet, MA (US)

(73) Assignee: Genzyme Corporation, Cambridge, MA (US)

( * ) Notice: Subject to any disclaimer, the term of this patent is extended or adjusted under 35 U.S.C. 154(b) by 98 days.

(21) Appl. No.: 09/746,310

(22) Filed: Dec. 20, 2000

(65) Prior Publication Data

US 2002/0077531 A1 Jun. 20, 2002

(51) Int. Cl.⁷ .................................................. A67B 1/00
(52) U.S. Cl. ........................ 600/232; 600/201; 600/210; 600/235
(58) Field of Search ............................ 600/232, 231, 600/233, 235, 228, 201, 227, 210

(56) References Cited

U.S. PATENT DOCUMENTS

| | | |
|---|---|---|
| 2,594,086 A | 4/1952 | Smith |
| 3,638,973 A * | 2/1972 | Poletti |
| 3,710,783 A | 1/1973 | Jascalevich |
| 3,858,578 A | 1/1975 | Milo |
| 4,143,652 A | 3/1979 | Meier et al. |
| 4,491,435 A | 1/1985 | Meier |
| 4,726,356 A | 2/1988 | Santilli et al. |
| 4,863,133 A | 9/1989 | Bonnell |
| 5,092,551 A | 3/1992 | Meier |
| 5,231,974 A | 8/1993 | Giglio et al. |

(List continued on next page.)

FOREIGN PATENT DOCUMENTS

| | | |
|---|---|---|
| CA | 2216893 | 2/1999 |
| EP | 0411586 | 2/1991 |

(List continued on next page.)

OTHER PUBLICATIONS

Angelini, G.D., A Simple, Inexpensive Method of Heart Retraction During Coronary Artery Bypass Surgery, Ann. Thorac. Surg., Aug. 1988, pp. 246–247, vol. 46, From the Dept. of Cardiac Surgery, University Hospital of Wales Cardiff, United Kingdom.

(List continued on next page.)

Primary Examiner—Pedro Philogene
(74) Attorney, Agent, or Firm—Richard D. Allison; Thomas DesRosier

(57) ABSTRACT

The present invention relates to surgical retractors and devices for stabilizing a predetermined area of the body during a surgical procedure, more particularly to surgical retractors and stabilizing devices used in connection with minimally invasive coronary artery bypass grafting surgical procedures, and more specifically to surgical retractors and stabilizing devices especially configured for use with each other for such surgical procedures wherein the retractor includes an external rail system which enables the surgeon to position a stabilization arm having first and second shaft segments on either of the arms or the rack segment of the retractor and also includes a connector which is spaced apart from the sled member and stabilization device to releasably control the movement and rotation of the stabilization device with respect to the stabilization arm and the rotation of the stabilization arm with respect to the retractor actuation of a single knob or actuator.

32 Claims, 8 Drawing Sheets

U.S. PATENT DOCUMENTS

| | | | |
|---|---|---|---|
| 5,452,733 A | 9/1995 | Sterman et al. |
| 5,503,617 A | 4/1996 | Jako |
| 5,509,890 A | 4/1996 | Kazama |
| 5,513,827 A | 5/1996 | Michelson |
| 5,616,117 A | 4/1997 | Dinkler et al. |
| 5,667,481 A | 9/1997 | Villalta et al. |
| 5,727,569 A | 3/1998 | Benetti et al. |
| 5,730,757 A | 3/1998 | Benetti et al. |
| 5,749,892 A | 5/1998 | Vierra et al. |
| 5,782,746 A | 7/1998 | Wright |
| 5,807,243 A | 9/1998 | Vierra et al. |
| 5,810,721 A | 9/1998 | Mueller et al. |
| 5,836,311 A | 11/1998 | Borst et al. |
| 5,846,193 A | 12/1998 | Wright |
| 5,846,194 A | 12/1998 | Wasson et al. |
| 5,865,730 A | 2/1999 | Fox et al. |
| 5,875,782 A | 3/1999 | Ferrari et al. |
| 5,888,247 A | 3/1999 | Benetti |
| 5,894,843 A | 4/1999 | Benetti et al. |
| 5,899,425 A | 5/1999 | Corey, Jr. et al. |
| 5,908,382 A | 6/1999 | Koros et al. |
| 5,927,284 A | 7/1999 | Borst et al. |
| 5,947,896 A | 9/1999 | Sherts et al. |
| 5,957,835 A | 9/1999 | Anderson et al. |
| 5,967,973 A | 10/1999 | Sherts et al. |
| 5,976,080 A | 11/1999 | Farascioni |
| 5,984,864 A | 11/1999 | Fox et al. |
| 6,063,021 A | 5/2000 | Hossain et al. |
| 6,213,941 B1 * | 4/2001 | Benetti et al. |
| 6,231,506 B1 * | 5/2001 | Hu et al. |
| 6,338,738 B1 * | 1/2002 | Bellotti et al. |
| 6,379,297 B1 * | 4/2002 | Furnish et al. |

FOREIGN PATENT DOCUMENTS

| | | |
|---|---|---|
| EP | 0791330 | 8/1997 |
| EP | 0820721 | 1/1998 |
| FR | 1019217 | 1/1953 |
| GB | 1520832 | 8/1978 |
| WO | WO 95/17127 | 6/1995 |
| WO | WO 98/27869 | 7/1998 |
| WO | WO 98/48704 | 11/1998 |
| WO | WO 00/10466 | 3/2000 |
| WO | WO 00/15119 | 3/2000 |
| WO | WO 00/42921 | 7/2000 |
| WO | WO 00/66008 | 11/2000 |
| WO | WO 01/03585 | 1/2001 |

OTHER PUBLICATIONS

Badellino, Michael M., The Cardiac Rag, Simple Exposure of the Heart, Texas Heart Institute Journal, 1988, pp. 134–135, vol. 15, No. 2, Temple University, Philadelphia, Pennsylvania, USA.

Bugge, M., A New Internal Mammary Artery Retractor, Thorac. Cardiovas. Surgeon, 1990, pp. 316–317, vol. 38, Georg Thieme Verlag Stuttgart, New York, USA.

Delrossi, A..J. et al., A New Retractor to Aid in Coronary Artery Surgery, The Annals of Thoracic Surgery Jul. 1983, pp. 101–102, vol. 36, No. 1, Deborah Heart and Lung Center, Browns Mills, NJ, USA.

Eguchi, Akiharu, Heart Retractor for Use in Anastomosis in Coronary Artery By–Pass Surgery, Japanese Journal of Thoracic Surgery, 1987, pp. 1–2, vol. 40, No. 1 Translations, USPTO, Dec. 18, 1997 Akiko Smith.

Matsuura, Akio et al., A New Device for Exposing the Circumflex Coronary Artery, Ann. Thorac. Surg., 1995, pp. 1249–1250, vol. 59, Nagoyo University School of Medicine, Nagoya, Japan.

Parsonnet, Victor et al., Self–Retaining Epicardial Retractor for Aortocoronary Bypass Surgery, The Journal of Thoracic and Cardiovascular Surgery, Current Technique, Dec. 1978, pp. 629–630, Newark Beth Israel Medical Center, Newark, NJ, 1979 The C. V. Mosby Co.

Robicsek, Francis Aortic Spoon–Jaw Clamp for Aor-to–Saphenous Vein Anastomosis, J. Card. Sug., 1995, pp. 583–585, vol. 10, Carolinas Medical Center, Charlotte, NC, Futura Publ. Co.

Rousou, John A.. et al., Cardiac Retractor for Coronary Bypass Operation, How to Do It, Exposure for Coronary Bpass, Ann. Thorac. Surg., 1991, pp. 877–878, vol. 52, Dept. of Surgery, Baystate Medical Center, Springfield, MA.

Roux, D. et al., New Helper Instrument in Cardiac Surgery, Ann. Thorac. Surg., 1989, pp. 595–596, vol. 48, Cedex, France.

Westaby, Stephen et al., Less Invasive Coronary Surgery: Consensus From the Oxford Meeting, Ann. Thorac. Surg., 1996, pp. 924–931, vol. 62, The Society of Thoracic Surgeons, Published by Elsevier Science Inc., Oxford Heart Center, Oxford Radcliffe Hospital, Oxford, England.

* cited by examiner

SEGMENTED ARM ASSEMBLY FOR USE WITH A SURGICAL RETRACTOR AND INSTRUMENTS AND METHODS RELATED THERETO

FIELD OF INVENTION

The present invention relates to surgical retractors and devices for stabilizing a predetermined area of the body during a surgical procedure, more particularly to surgical retractors and stabilizing devices used in connection with an improved segmented arm assembly that is preferably used in coronary artery bypass grafting surgical procedures, and more specifically to a segmented arm that is used with various surgical retractors and stabilization devices for use in various surgical procedures.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system affecting blood flow to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, especially when multiple grafts are needed.

In the coronary artery bypass graft procedure, the surgeon either removes a portion of a vein from another part of the body for grafting or detaches one end of an artery and connects that end past the obstruction in the coronary artery while leaving the other end attached to the arterial supply. When using a vein from another part of the body, the surgeon installs this portion at points that bypass the obstruction. In both cases, the objective is to restore normal blood flow to the heart.

In addition, when using this technique the surgeon makes a long incision down the middle of the chest, saws through the sternum, spreads the two halves of the sternum apart and then performs several procedures necessary to connect the surgical patient to a cardiopulmonary bypass machine to continue the circulation of oxygenated blood to the rest of the body while the heart is stopped and the graft is being sewn in place. Although such a procedure is one common technique for treatment, the procedure is lengthy, traumatic, considerably more expensive and can damage the heart, the central nervous system and the blood supply.

Interventional techniques, such as percutaneous transluminal angioplasty (PTCA) have gained popularity as the method of choice for therapy of atherosclerosis occlusions for several reasons. The transluminal approach is a minimally invasive technique that subjects the patient to less trauma and less recovery time, especially when compared to bypass grafts which utilize homologous tissue, such as saphenous vein grafts. Also, the patient often suffers complications at the donor site of the graft that may be worse than the sternotomy and anastomosis.

Although PTCA procedures are often successful, complications such as restenosis or thrombosis and embolism can occur. Restenosed vessels may often require surgical intervention for correction. The surgical correction of restenosis like the conventional coronary bypass surgical procedure requires the heart to be stopped and the patient placed on a heart/lung bypass machine during the procedure.

In recent years, and in an effort to reduce expense, risk and trauma to the patient, physicians have turned to minimally or less invasive surgical approaches to the heart, such as intercostal and endoscopic access to the surgical site. With such procedures, the heart is beating during the surgical procedure. Thus, there is no need for any form of cardiopulmonary bypass and there is no need to perform the extensive surgical procedures necessary to connect the patient to such a bypass machine.

Such attempts at performing minimally invasive bypass grafting on a beating heart, however, have been thought of as being tedious, dangerous and difficult because of the delicate nature of the surgical procedure, the lack of adequate access through a reduced surgical field, and the lack of a way to adequately stabilize and reduce tissue movement at the graft site. Because these procedures are performed while the heart muscle is continuing to beat, the blood continues to flow and the heart continues to move in three dimensional movement while the surgeon is attempting to sew the graft in place. Also, the surgical procedure to install the graft requires placing a series of sutures through an extremely small vessel and onto tissue that continues to move during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart or together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 5,875,782 granted to Ferrari et al.; U.S. Pat. No. 6,033,362 granted to Cohn; U.S. Pat. No. 6,102,854 granted to Cartier et al.; U.S. Pat. No. 5,947,896 granted to Sherts et al.; and U.S. Pat. No. 5,894,843 granted to Benetti et al. various devices for stabilizing the predetermined area on a heart or other organ of a patient to enable a surgical procedure on a beating heart. These devices include various stabilization members and an elongated arm. The arm segments can be movably attached to a rib retractor so that a person is not required to hold the arm segment. In one disclosed embodiment, the apparatus further includes a device to hold a bifurcated member in a position against the surface of the heart sufficiently so that a stabilizing force is applied against the heart and contraction of the heart does not cause either vertical or horizontal motion at the target site during the surgical procedure.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the arm segment and the suction device may be locked into position against the surface of the heart.

It is therefore desirable to provide a new system and devices related thereto for stabilizing a predetermined area of the body, such as the heart and methods related thereto. It is particularly desirable to provide such a system and devices thereto that are less complex and more user friendly in comparison to prior art devices. Such systems and devices thereto preferably are simple in construction and less costly than prior art devices.

SUMMARY OF THE INVENTION

The present invention features a system for retracting, stabilizing or manipulating a predetermined area of a body. The system includes a sled assembly for use with a surgical retractor, a stabilization arm system or apparatus and a tissue support or stabilization device, and methods of use related thereto. Also featured is a system that supports any of a number of surgical implements, for example a diaphragm retractor, a valve retractor, a light source or suction device for use during a surgical procedure.

The stabilization system and related devices and apparatuses thereto that are featured herein are particularly advantageous for use in performing off-pump coronary artery bypass grafting procedures in which the heart remains beating during the surgical procedure and/or valve surgery where the heart is stopped. One advantage of the present invention relates to the versatile use of a segmented arm system which is connected to an arm or rack section of the retractor and also retains a stabilization device or surgical implement in a desired position. The use of the external rail system on the retractor allows the stabilization arm system to be attached to the retractor at any desired location and does not require that the stabilization arm system be slid on from an end of an arm or specially attached in certain specific locations. Additionally, the segmented arm assembly of the present invention allows for a full range of three dimensional motion of the stabilization device or surgical instrument which is controlled by a single knob that is spaced apart from each of the retractor and stabilization device. The segmented arm assembly is also easily and conveniently manipulated by the surgeon and is movable so as not to obstruct the surgeon's view of the desired target location.

In a general aspect, the stabilization system of the present invention is preferably used for stabilizing a predetermined area the heart tissue of a patient. This system preferably includes a retractor, a stabilization device for locally stabilizing the predetermined area and/or a surgical instrument as well as a stabilization arm system that functionally secures the stabilization device to the retractor. The retractor preferably includes a rail system having two arms and a rack segment. The rack segment interconnects the two arms, for selectively spacing the two arms from each other and for maintaining the two arms in a desired fixed relationship. In a preferred form of the present invention, the two arms and rack segment are configured to receive the sled member of the stabilization arm system at the desired location thereon.

The stabilization device preferably includes devices of the type commonly known as the Cohn Cardiac Stabilizer or the Immobilizer marketed by the Genzyme Corporation of Cambridge, Mass., although horseshoe or suction type devices may also be used. The preferred form of the stabilization device is a generally square, rectangular or teardrop shaped member having a planar surface with centrally located opening therein. This opening is the area through which the surgeon performs the anastomosis or other procedure on the tissue of the beating heart. The stabilization device is preferably a multiple piece member so that once the anastomosis is completed, the pieces or an end portion thereof may be separated to remove the device from around the anastomosis. As described more fully below, flexible tapes are preferably sutured through the tissue and then threaded through the stabilizing device to provide temporary vessel occlusion. Once the stabilization device is positioned in the desired orientation and location in contact with the tissue, the flexible tapes are then pulled snug through the opening of the stabilization device to provide a system that captures the predetermined area of the tissue.

The stabilization arm system preferably includes an elongated arm having a proximal connector for attachment to the retractor and a distal connector thereon for releasably connecting the stabilization device or surgical instrument to the elongated arm. The distal connector allows the stabilization device to be pivotally and slidably moved to a desired position into contact with the predetermined area of the tissue of the patient. The stabilization arm system of this embodiment also preferably includes a pivotal segment located approximately midway along the length of the arm. The pivotal segment provides an additional location for relative movement of the stabilization device as well as providing a common location for fixing the desired position of the stabilization arm system along the retractor and relative to the stabilization device. Additionally, the pivotal segment allows the user to position at least a portion of the arm segment away from the desired surgical site so that the arm system does not obstruct the view of the surgeon or the assistant while providing sufficient leverage to provide a stable surgical site and to allow access to various locations on the heart of the patient. The stabilization arm system further includes the sled member connected to the proximal connector for removably securing the stabilization arm system to at least one of the rails on the retractor arms and/or the rack segment of the retractor and which is preferably slidable along the retractor. The stabilization arm system preferably includes a pivotal mounting mechanism which selectively engages the sled member. In the preferred form of this invention, the pivoting movement of the sled member relative to the arm is controlled by operation of the pivoting segment.

According to one aspect of the present invention, the arms of the retractor are preferably configured with a front edge and a step in the top surface thereof to form an elongated rail surface along substantially the entire length thereof. The step is preferably spaced apart a predetermined and consistent distance from the front edge and is also located on the interconnecting or rack segment of the retractor. Also, the sled assembly is preferably configured to removably engage the front edge and the step at any desired location on one or more of the arms or the rack segment of the retractor. The sled member preferably includes a lever for selectively engaging the step and front edge on the arm or rack segment of the retractor so the sled member is removably and slidably secured to the arms or the rack segment.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein.

DESCRIPTION OF THE PREFERRED EMBODIMENT

Figure 1A:
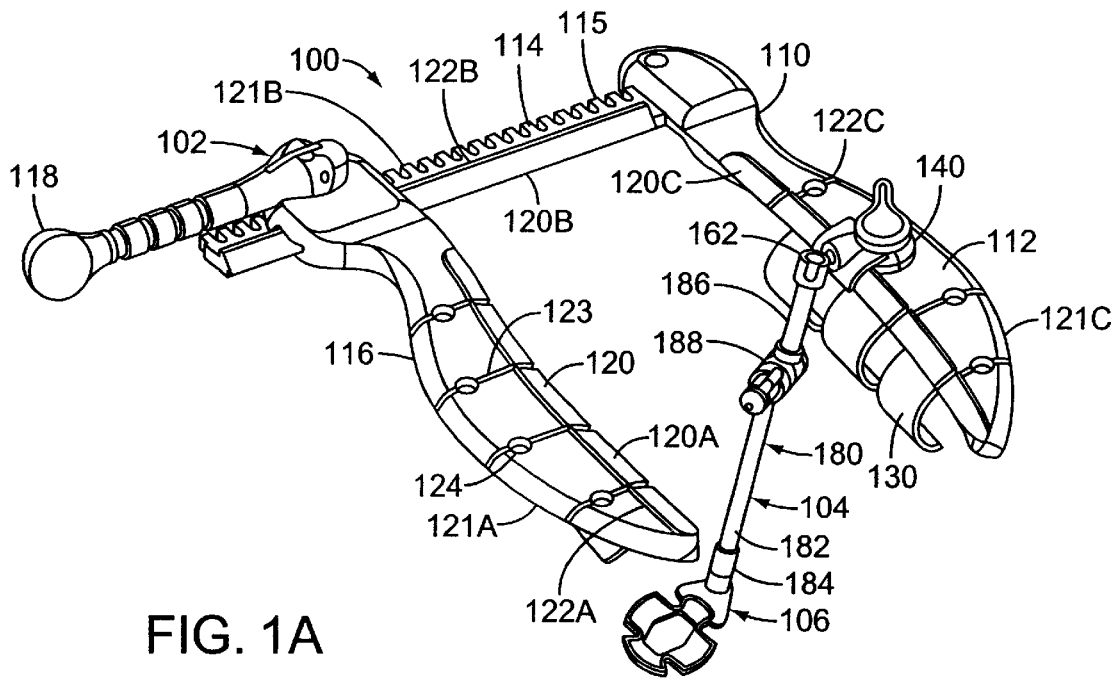
FIGS. 1A and 1B are perspective views of the preferred form of the stabilization system that assists in the stabilization of a predetermined area of a body according to a first aspect of the present invention wherein the stabilization arm system is shown attached to an arm of the retractor and in an extended configuration in FIG. 1A and in a non-extended configuration in FIG. 1B.
Figure 1B:
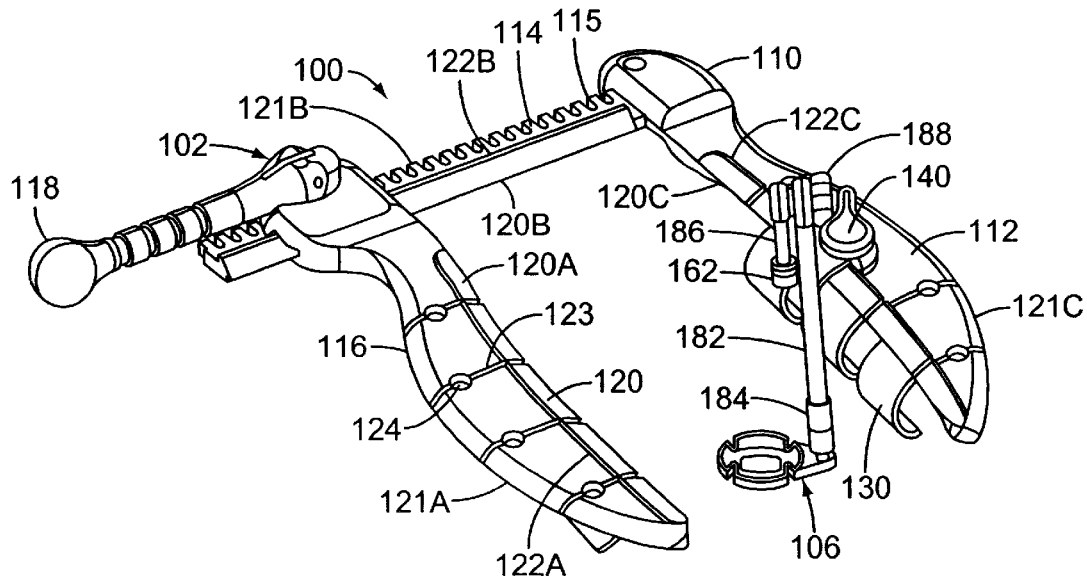
Figure 2A:
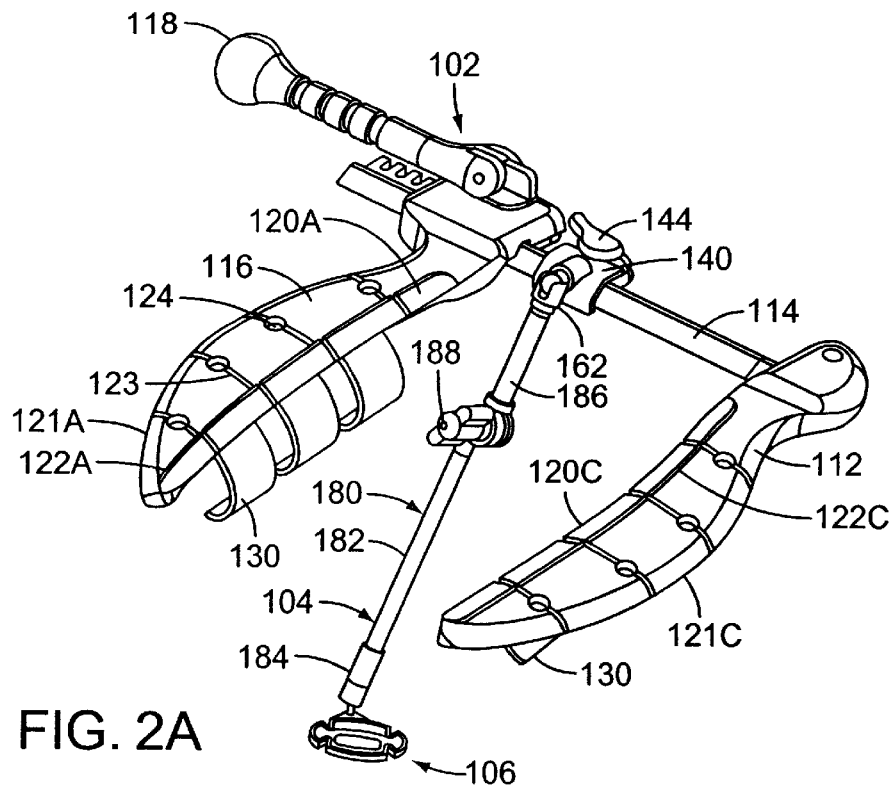
FIGS. 2A and 2B are perspective views of the preferred form of the stabilization system that assists in the stabilization of a predetermined area of a body according to a first aspect of the present invention wherein the stabilization arm system is shown attached to the rack segment of the retractor and in an extended configuration in FIG. 2A and in a nonextended configuration in FIG. 2B.
Figure 2B:
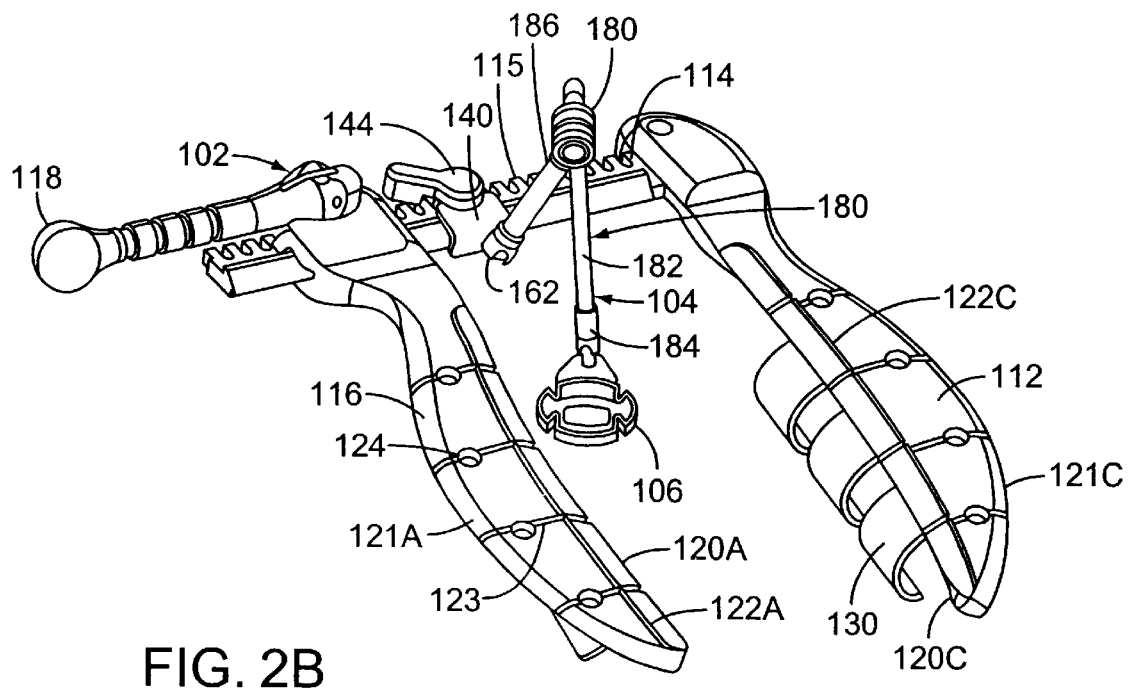
Figure 3A:
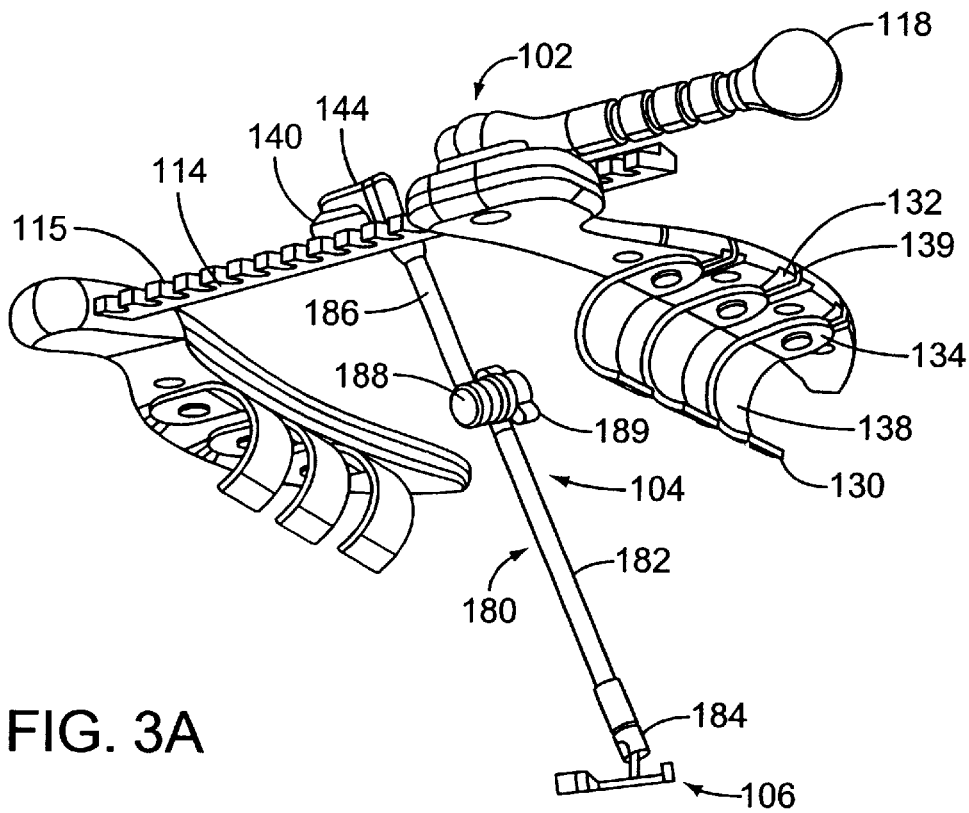
FIGS. 3A and 3B are bottom perspective views of the preferred form of the stabilization system that assists in the stabilization of a predetermined area of a body according to a first aspect of the present invention wherein the stabilization arm system is shown attached to the rack segment of the retractor and in an extended configuration in FIG. 3A and in a non-extended configuration in FIG. 3B.
Figure 3B:
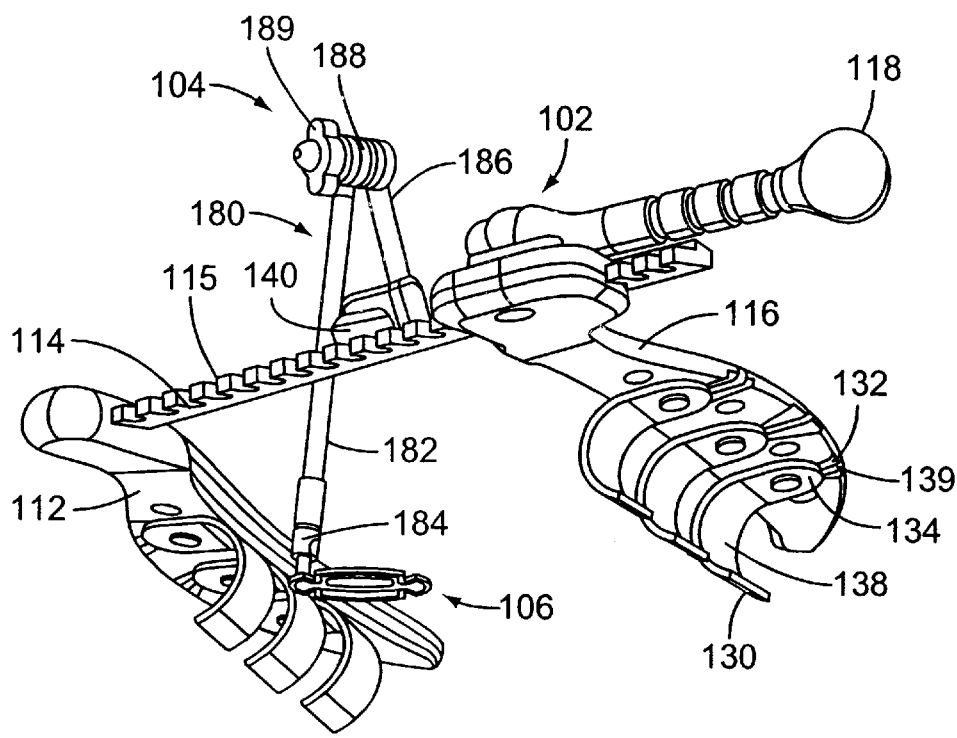
Figure 4A:
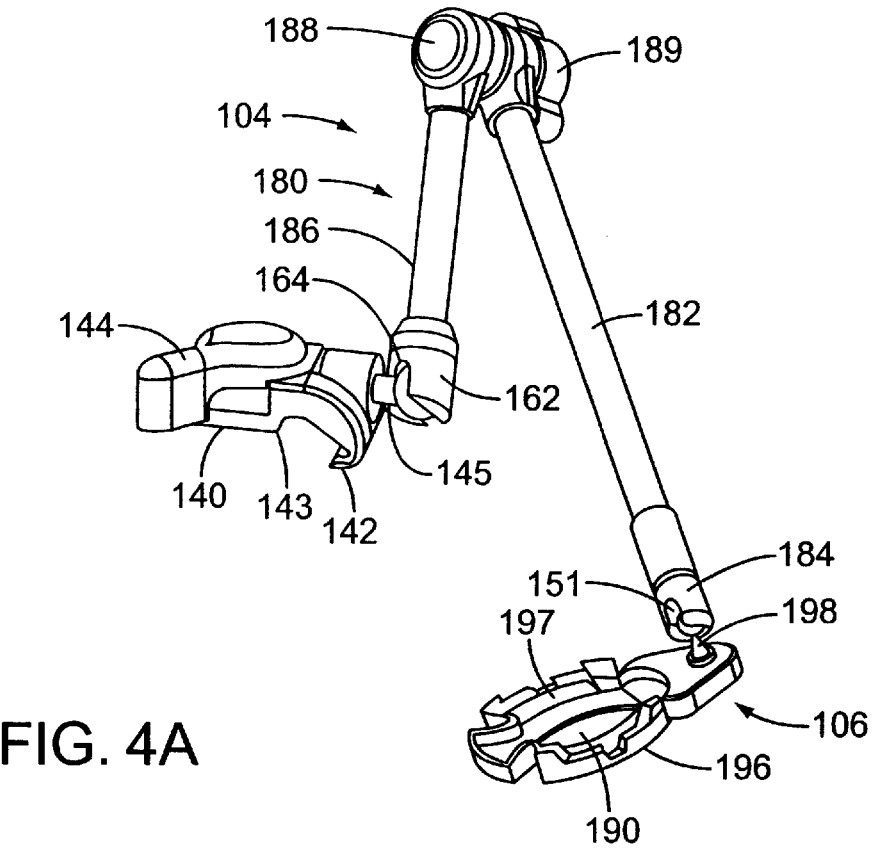
FIGS. 4A and 4B are perspective views of the stabilization arm system and a stabilization device of the present invention wherein the stabilization arm system is shown in a pair of non-extended configurations.
Figure 4B:
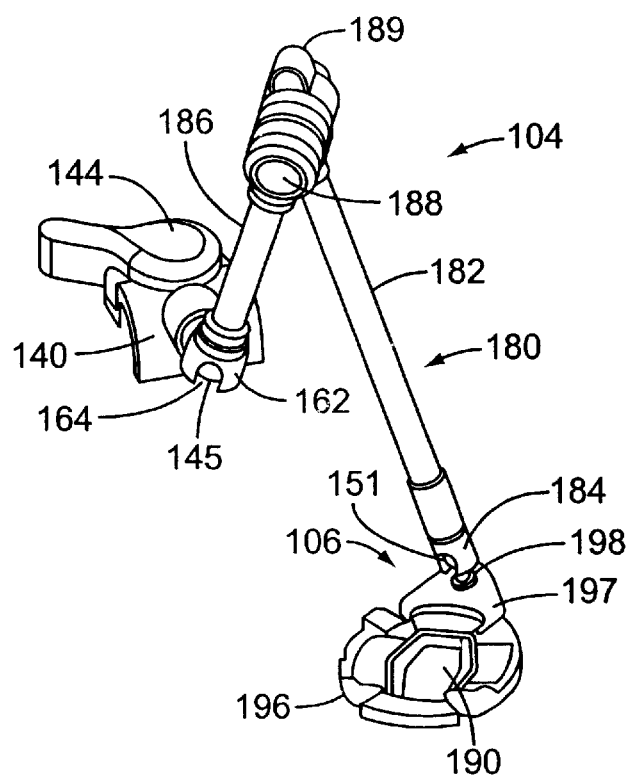
Figure 5:
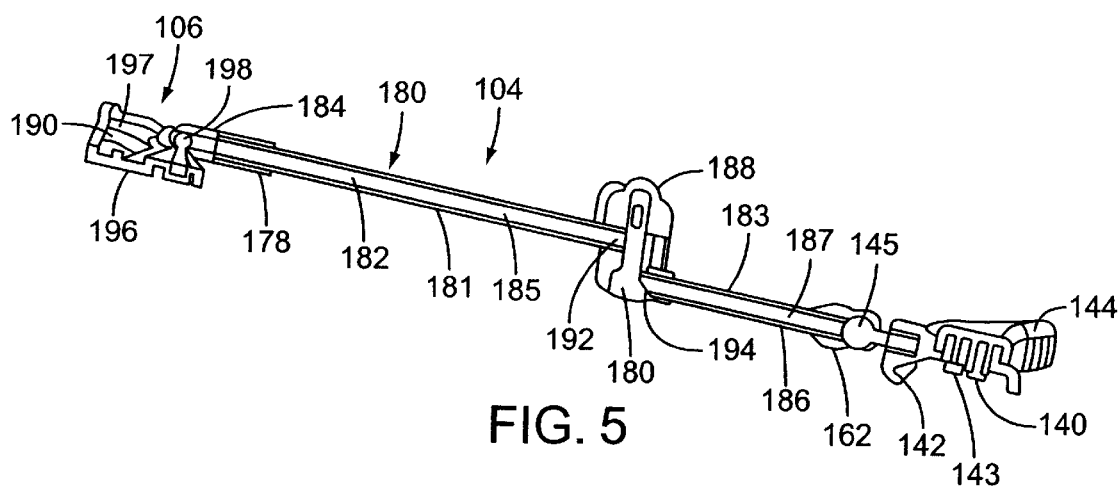
FIG. 5 is an enlarged perspective view, partially in cross section, of the stabilization arm system, stabilization device and sled member of the present invention.
Figure 6A:
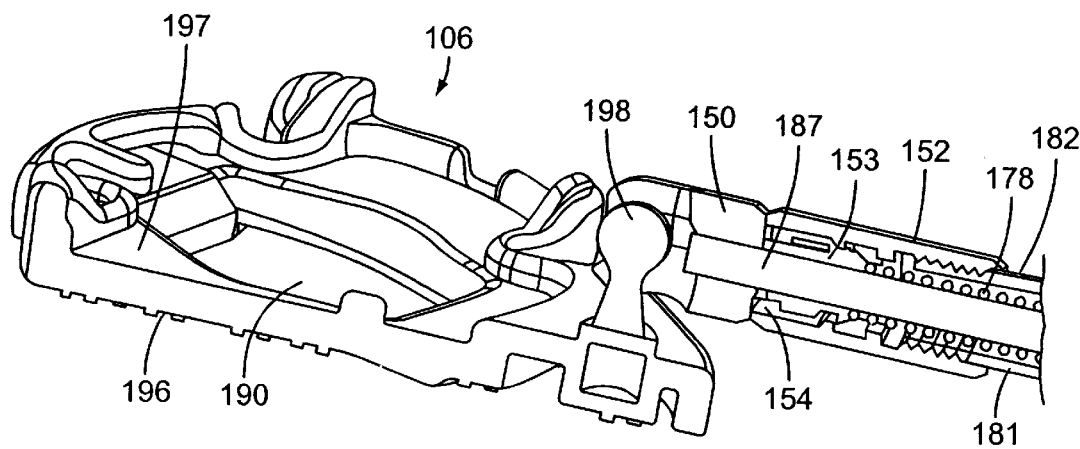
FIGS. 6A and 6B are enlarged perspective views, partially in cross section, of the distal portion of the stabilization arm and stabilization device of the present invention showing the stabilization arm system and stabilization device in a movable and a fixed position relative to the stabilization device, respectively.
Figure 6B:
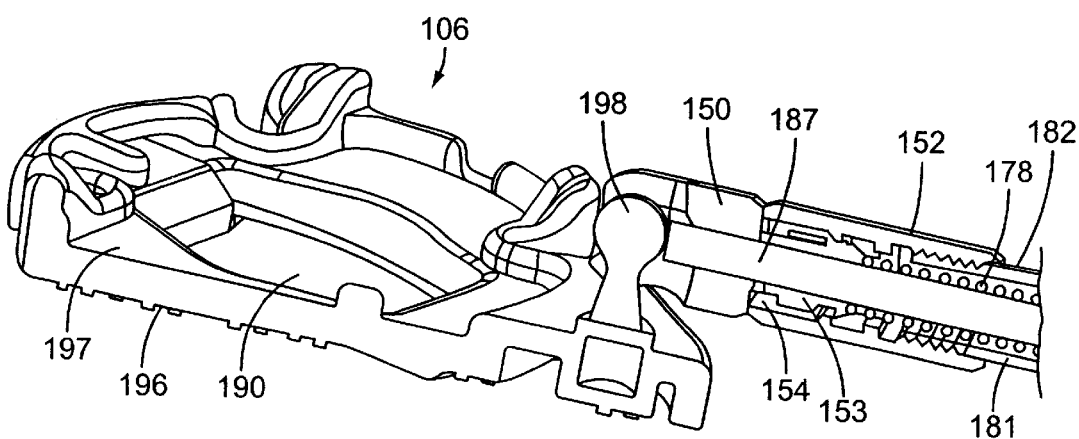
Figure 7A:
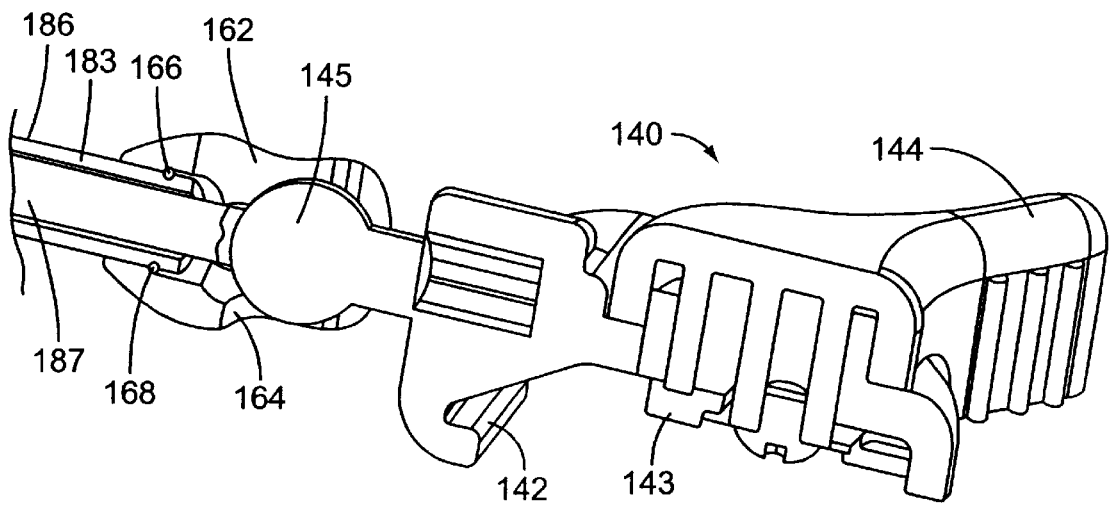
FIGS. 7A and 7B are enlarged perspective views, partially in cross section, of the proximal portion of the stabilization arm and the sled member of the present invention showing the stabilization arm system and stabilization device in a movable and a fixed position relative to the sled member, respectively.
Figure 7B:
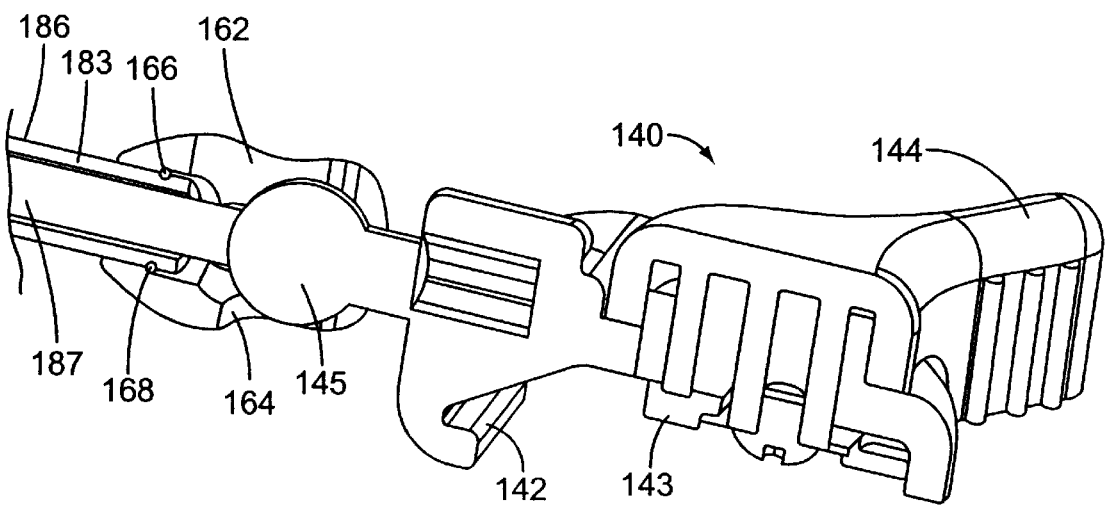
Figure 8A:
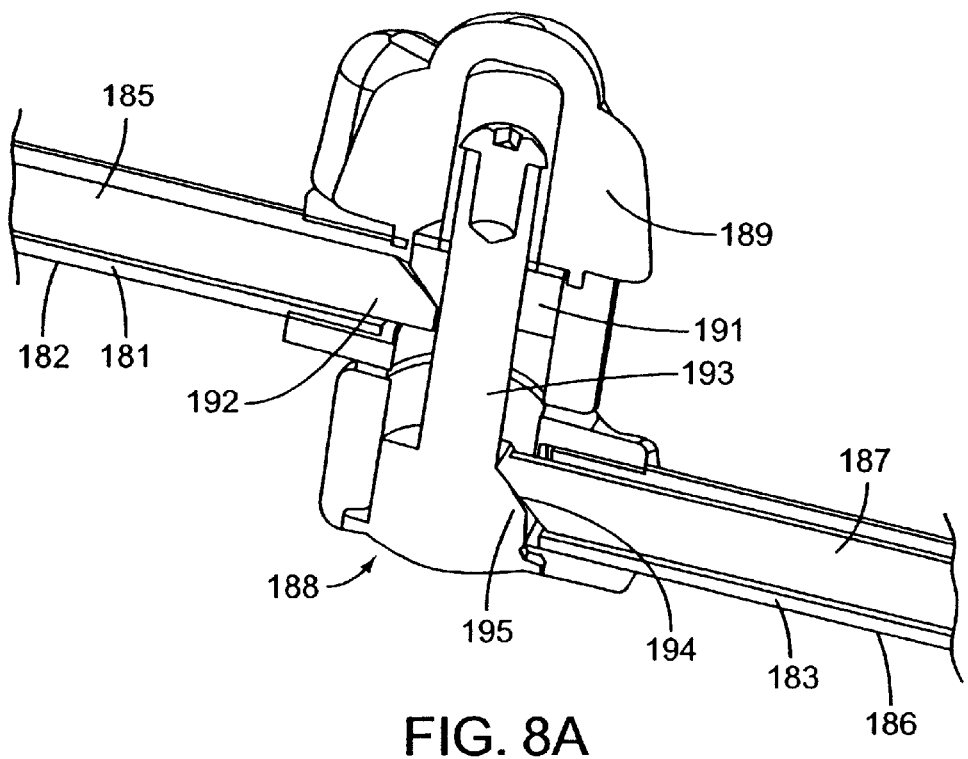
FIGS. 8A and 8B are enlarged perspective views, partially in cross section, of the movable arm assembly of the stabilization arm system of the present invention showing the stabilization arm system in a movable and a fixed position relative to the sled member and stabilization device.
Figure 8B:
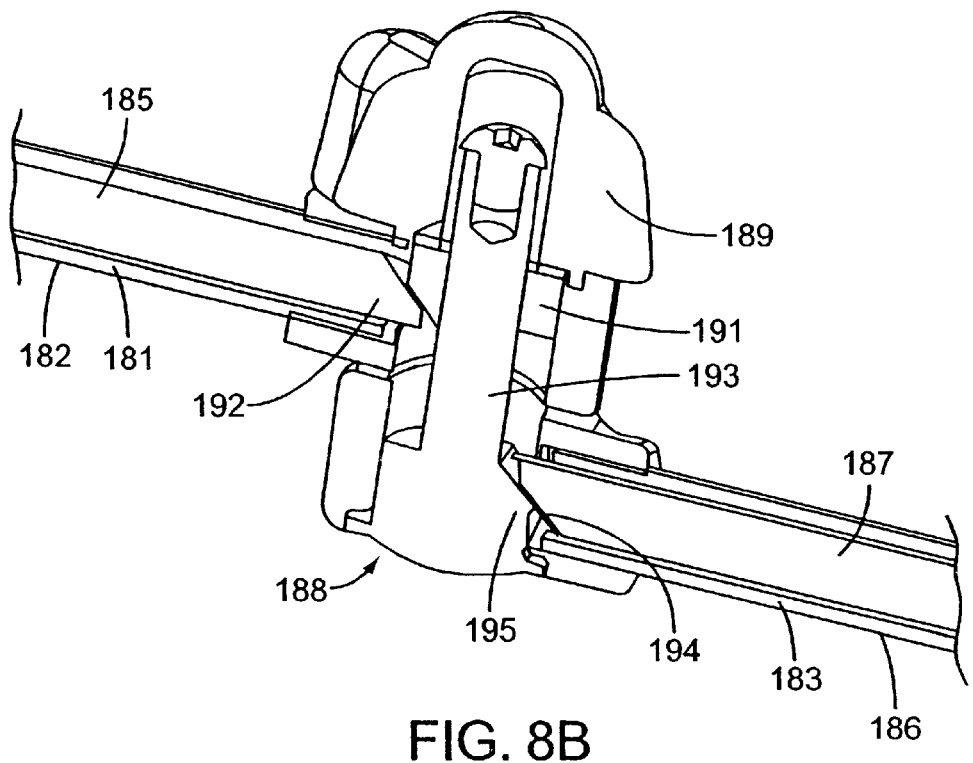

Systems for stabilizing the heart of a patient are particularly useful for various suturing techniques or procedures. One example of this type of procedure is the performance of an anastomosis for a bypass graft during cardiac surgery. In this type of procedure, the physician is attempting to suture the circumference of a blood vessel that may be about 1 mm to a moving blood vessel on the surface of the heart. Another area of use of the present invention may be in brain surgery, heart valve surgery or various types of blood vessel surgery where access and stability are critically important to avoid disastrous consequences or where it is desirable to have a precisely defined surgical field. One skilled in the art will appreciate that the present invention, although advantageously suited for heart surgery, can be used at any location on or within the body where tissue stabilization, retraction or isolation of a predetermined area is desired. This includes, but is not limited to, the liver, kidneys, bladder, stomach, intestines, brain and vascular and other soft tissue surgery. Additionally, one skilled in the art will appreciate, as hereinafter described, that the supporting components of the system can be adapted so that any surgical instrument or device can be self-supported during a surgical procedure.

Referring now to the various figures of the drawings wherein like reference characters refer to like elements, there are shown various views of preferred and alternate forms of a stabilization system 100 according to the present invention. As described more fully below, the embodiments of the present invention are intended for use in contributing to the accessibility or stabilization of a predetermined area of a body such as an area of a heart or other organ of a patient and to enable the physician to perform a surgical operation or procedure on a patient. The stabilization system 100 is particularly useful in connection with single or multiple vessel off-pump coronary artery bypass surgery on a beating heart through a sternotomy or mini-sternotomy incision although various other uses may be envisioned by a person skilled in this art.

A surgeon may use the stabilization system 100 to apply a slight contacting or compressive force on the heart in the area where the surgical procedure will occur so the tissue will be captured and the heart's movement at that specific area is diminished. In a preferred form of this invention, the stabilization system 100 is used in combination with flexible tapes or sutures or other mechanical means so that the surface of the heart is stabilized using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is restricted as desired by the surgeon.

Referring specifically to the drawings, the stabilization system 100 according to the present invention includes a retractor 102, an arm system or stabilization arm 104 and a stabilization device 106. The retractor 102 is specifically configured so the stabilization arm 104 can be secured thereto via a sled member 140. The retractor 102 preferably includes a rigid L-shaped member 110 having a first arm segment 112 and a rack segment 114. The retractor 102 also includes a movable second arm segment 116 having a handle 118 thereon which is movably associated with the L-shaped member 110.

The preferred form of the stabilization device 106 is generally a tear drop or rectangular shape having an opening or window area 190 therein. The stabilization device 106 preferably includes a first surface 196 that is generally planar and may include a textured surface thereon to facilitate the engagement between the stabilization device and the tissue of the predetermined area or the heart of the patient. The second surface 197 of the stabilization device 106 preferably includes a post member 198 extending therefrom.

The post member 198 is preferably releasably and rotatably engaged by the distal connector 184 on the first shaft segment 182 as described more fully below.

Figure 9:
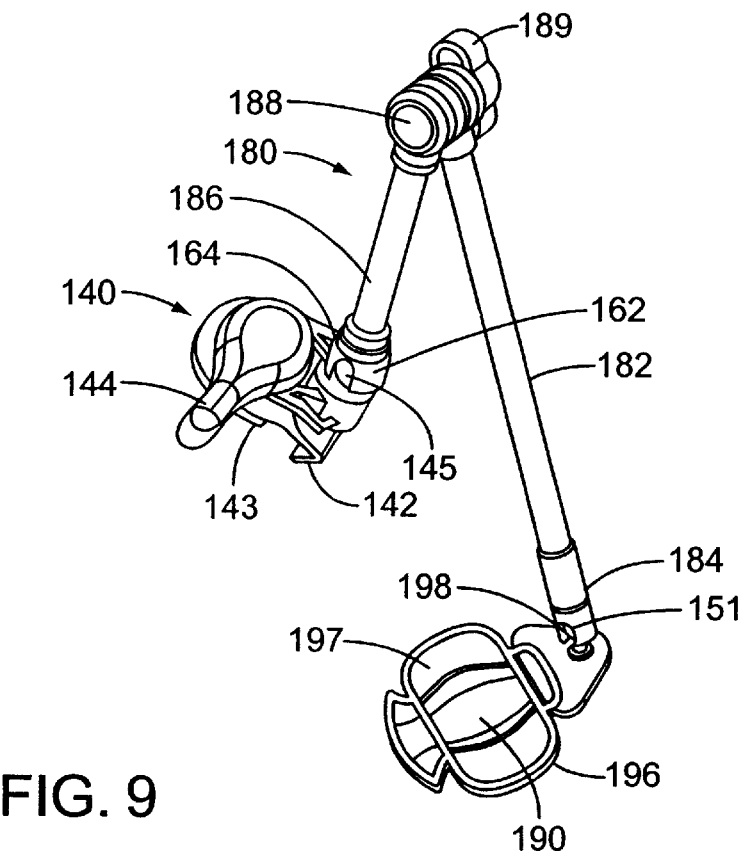
FIG. 9 is a perspective view of an alternate form of the stabilization arm system and stabilization device of the present invention that assists in the stabilization of a predetermined area of a body according to a first aspect of the present invention wherein the stabilization arm system is shown in a non-extended configuration.

The stabilization arm or sub-system 104 preferably includes an elongate arm segment 180 that interconnects the retractor 102 and the stabilization device 106. The arm segment 180 preferably includes a first shaft segment 182 having a distal connector 184 thereon. The distal connector 184 is preferably fully rotatable around the distal end portion of the first shaft segment 182 and also pivotally and removably retains the stabilization device 106 thereon. The arm segment 180 also includes a second shaft segment 186 having a proximal connector 162 that is preferably fully rotatable about the proximal end portion of the second shaft segment 186 and is attachable to the retractor 102 by a connector such as a mounting mechanism or sled member 140. The proximal connector 162 of the second shaft segment 186 preferably pivotally engages a ball member 160 located on the sled member 140 and may be positioned in various orientations relative thereto including parallel or perpendicular thereto. In a preferred form of the present invention, the ball member 160 extends laterally from the sled member 140 as shown in FIGS. 1–8, although the ball member 160 may also be an upstanding member as shown in FIG. 9.

The proximal end of the first shaft segment 182 and the distal end of the second arm segment 186 are preferably interconnected by an actuation member such as a movable knob assembly 188 thereon that is pivotal with respect to the elements of the arm segment 180 to allow the pivotal movement between the first shaft segment 182 and the second shaft segment 186. The actuation member is described herein as a movable knob assembly although a lever, sliding member, lock assembly, screw member, hydraulic assembly, thumb ratchet, toggle switch, key, worm gear or similar component may be used to perform the desired features and function described more fully herein. Similarly, various other mechanisms may be used to translate the movement of the actuation member to the distal and proximal end portions, including hydraulic members, cables, sliding members, toggles or similar mechanisms. Therefore, in addition to controlling the relative movement between the first shaft segment 182 and the second shaft segment 186, the movable knob assembly 188 preferably also controls the pivotal movement of the arm segment 180 relative to the sled member 140 and also allows the stabilization device 106 to be fixed, removable and/or pivotal with respect to the arm segment 180 by manipulating the movable knob assembly.

The first and second shaft segments of the arm segment 180 preferably include hollow and rigid tubular members, 181 and 183 respectively. Additionally, each of the first and second shaft segments include elongate movable plunger rods, 185 and 187, that are movable between first and second positions relative to the tubular members. The first and second shaft segments, 182 and 186, are preferably straight and approximately equal in length. Alternately, the first and second shaft segments may be of unequal length and one or both of the shaft segments may be curved. The length of the shaft segments are chosen to provide the user with increased versatility in the placement of the stabilization device 106 for the desired surgical procedure while also allowing the movable knob assembly 188 to be positioned to the side of or outside of the surgeon's view or the surgical field. The stabilization device 106 may be positioned in various locations in the surgical field and may be positioned to extend from either of the arms and/or rack segment of the retractor.

Therefore, it is important that the stabilization arm 104 extend a sufficient distance from the retractor arm or rack segment to a desired surgical site while also being adjustable so as not to obstruct the surgeon's view of the surgical site. A further consideration addressed by the present invention is the need for the stabilization arm to provide sufficient stability and strength to minimize movement of the stabilization device in each of the possible desired positions in the surgical field so that the stabilization device 106 is retained in the desired position when the first and second shaft segments are aligned linearly or when they are oriented at acute or obtuse angles.

The movable knob assembly 188 of the stabilization arm 104 preferably includes a knob 189 with a preferably free moving first cam element 191 and a screw member 193 with a preferably fixed second cam element 195. As shown, the knob 189 is movable generally perpendicular to the lengthwise dimension of the stabilization arm 104 and causes compression of the movable knob assembly 188 along the screw member 193 to fix the pivotal movement of the first shaft segment 182 and the second shaft segment 186. Tightening of the movable knob assembly 188 also causes the movement of the first cam element 191 into contact with an angled end portion 192 of the plunger rod 185 associated with the first shaft segment 182. Movement of the first cam element 191 and the associated distal movement of the plunger rod 185 causes the tightening, and ultimately, the fixation of the stabilization device 106 relative to the stabilization arm 104. Additionally, tightening of the movable knob assembly 188 causes the second cam element 195 to contact and move the angled end portion 194 of the plunger rod 187 associated with the second shaft segment 184. The proximal movement of the second cam element 195 and the angled end portion 194 causes the second shaft segment to be fixed relative to the ball mount 160 on the sled member 140 to prevent pivotal movement between the second shaft segment 186 and the sled member 140.

The movable knob assembly 188 on the stabilization arm 104 allows the user to rotate the stabilization device 106 and arm segment 180 relative to the retractor 102 to orient the stabilization device in the desired three-dimensional location adjacent to the tissue to be manipulated. Clockwise rotation of the movable knob assembly 188 causes the knob 189 to move distally along the screw member 193 and cause the lateral displacement of the movable plunger rods, 185 and 187. This movement of the movable plunger rods, 185 and 187 functions to tighten the connection between the first shaft segment 182 and the second shaft segment 186 as well as tightening the connection between the arm segment between the sled member 140 and the stabilization device 106. Counterclockwise rotation of the movable knob assembly 188 causes the knob 189 to move proximally along the screw member 193 to release the movable knob assembly 188 and loosen the connection between the first shaft segment 182 and the second shaft segment 186 as well as to loosen the connection between the arm segment and the sled member 140 and between the arm segment and the stabilization device 106 to allow for the movement between the various components.

The distal connector 184 on the arm segment 180 consists of a generally cylindrical member 150 having an elongate slot 151 extending through at least one side thereof. Alternately, the distal connector may be bulbous or pear shaped member. In the preferred form of the present invention, the distal connector 184 is preferably rotatable with respect to the arm segment 180 to provide increased versatility in the positioning of the stabilization device 106 although it is contemplated that these components may also be fixed with respect to each other. The distal connector 184 is retained on the distal end of the arm segment 180 by an outer sleeve 152 which extends between the distal end of the arm segment 180 and the proximal end of the distal connector 184. The outer sleeve 152 also surrounds an inner connector 153 that engages a groove 154 in the proximal end portion of the distal connector and abuts the distal end of the arm segment to provide a limited amount of frictional resistance to the rotational movement of the distal connector 184 with respect to the arm segment 180. The slot 151 of the distal connector 184 is sized to allow the post member 198 of the stabilization device 106 to pass laterally therethrough to allow the stabilization device to be easily mounted on or removed from the stabilization arm 104 through the slot 151.

As shown, the distal end of the distal connector 184 includes a portion that is slightly larger than the rest of the slot surface to allow the post member 198 to be fully rotatable therethrough to increase the range of motion of the stabilization device. This arrangement preferably prevents the post member 198 of the stabilization device 106 from passing distally from the slot 151 while increasing the range of motion and providing a centered position for the post member 198. This flexibility in positioning allows the surgeon to readily position the stabilization device 106 in the desired position and against nearly any surface of the heart of the patient. The distal movement of the first cam element 191 and the plunger rod 185 in the first shaft segment 182 causes the tightening, and ultimately, the fixation of the stabilization device 106 relative to the stabilization arm 104. The distal movement of the plunger rod 185 against the post member 198 of the stabilization device 106 causes the post member 198 to press against the lower lip surfaces on the distal surface of the slot 151 of the distal connector 184 to preferably fixedly retain the post member 198 therein and prevent further movement of the stabilization device.

Rotation of the movable knob assembly 188 in a counterclockwise direction with respect to the arm segment 180 causes the angled end 192 of the plunger rod 185 to move proximally in the tubular member 181. This proximal movement occurs because the spring member 178 pushes against a portion of the plunger rod 185 and causes the distal end of the plunger rod 185 to move proximally away from the slot 151 and the post member 198 of the stabilization device 106. This proximal movement of the distal end of the plunger rod 185 allows for the rotation and/or release of the post member 198 of the stabilization device 106 from the distal connector 184. In the present invention, the spring member 178 is oriented to cause the plunger rod 185 to be normally spaced apart from the post member 198 of the stabilization device 106 to allow the stabilization member to readily removable therefrom as desired.

The generally cylindrical shape of the distal connector 184 and the opening in the slot 151 optimize the connection between the distal connector 184 and the post member 198 of the stabilization device. This arrangement enables the post member to be selectively retained within the distal connector 184 while allowing pivotal and rotational movement therebetween. Furthermore, in the preferred form of the present invention, the post member 198 is preferably retained in the slot 151 of the distal connector 184 even when the plunger rod 185 is spaced apart from the slot 151. Additionally, the rotation of the distal connector 184 with respect to the first shaft segment 182 and the use of the spring member 178 provide for an increased versatility in the use of the tubular member 181 in the present invention. This increased versatility allows the user to further manipulate the arm segment and stabilization device to the desired location in the surgical field. This freedom of movement and versatility is desirable for the present invention where space is at a premium and the device must be as versatile as possible to accommodate the surgeons needs without undue experimentation.

The proximal connector 184 on the second shaft segment 186 of the arm segment 180 consists of an elongate member 164 that may be slightly bulbous to accommodate the ball member 160 of the sled member 140 therein. The proximal connector 184 preferably includes an elongate slot 164 extending through at least one side thereof. In the preferred form of the present invention, the proximal connector 162 is preferably rotatable with respect to the second shaft segment 186 to provide increased versatility in the positioning of the stabilization device 106 relative to the sled member 140. Although the preferred form of this invention provides a great deal of relative movement between the sled member and the proximal connector 162, it is contemplated that these components may also be fixed with respect to each other. The proximal connector 162 is retained on the proximal end of the arm segment 180 by an outer sleeve portion that extends over the proximal end of the arm segment 180. The outer sleeve portion is preferably retained on the second shaft segment 186 with an O-ring 166 that engages a groove 168 in the distal end portion of the proximal connector 162 and abuts the proximal end of the arm segment. It is anticipated that the proximal connector 162 may be configured in a manner similar to the configuration described herein for the distal connector 184 to provide the additional rotational movement of the distal connector 184 described herein for the proximal connector 162. The slot 164 of the proximal connector 162 is sized to allow the ball member 160 of the sled member to pass laterally therethrough to allow the proximal connector to be easily mounted on and moved relative to the sled member 140 through the slot 164.

As described briefly above, the retractor 102 preferably includes a handle 118 located on the second arm segment 116 and the handle 118 is rotatable for displacing the two arm segments 112,116 with respect to each other. In the preferred embodiment, rotation of the handle 118 causes a pair of posts or pinions to sequentially engage the teeth 115 located on the outer edge 121*b* of the rack segment 114 to increase or decrease the distance between the first and second arms 112 and 116. The handle preferably includes a projection on the bottom surface thereof and the projection fits in a slot located in the retractor adjacent to the arm and rack segment to allow the user to lock the handle into position once the arms are in the desired position. This feature is particularly useful where the retractor is reused for a relatively long period of time for multiple procedures because the pinions and teeth on the retractor will gradually wear due to the pressure from the chest of the patient. As the wear occurs, the pressure from the sternum may cause the arms to move towards each other unless the arms or handle are retained in a locked position. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth members 115 that engage the posts or similar tooth engaging members located in operative contact with the handle 118 of the second arm segment 116. It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112. It is within the scope of the present invention, however, for the retractor 102 to be configured or designed with any of a number of means known to those skilled in the art for selectively displacing the first and second arm segments, 112 and 116 in a parallel, obtuse or acute angled manner.

At least one arm segment and preferably each arm segment, 112 and 116 respectively, and the rack segment 114 of the retractor 102 are configured so as to each have a front edge surface 120a, 120b and 120c extending along the inner surface of each element of the retractor 102 such that the front edges of each of the arms and the rack segment face each other. The retractor 102 also preferably includes an outer edge surface 121a, 121b and 121c extending along the outer surface of the first and second arms, 112 and 116 respectively, of the retractor 102. A step surface 122a, 122b and 122c extends along the top surface of the first and second arms, 112 and 116 respectively, and the rack segment 114 in a spaced apart relationship with respect to the front edges of each of the surfaces of the first and second arms and the rack segment to form an elongate lip or external rail surface on the arms and rack segment of the retractor. The step surface 122a–c is preferably located a preset distance back from the front edge and forms an acute angle facing away from the front edge thereof on each of the arms and the rack segment. As described hereinafter, the front edge surfaces 120a–c and the step surfaces 122a–c on the top surface of the arms and rack segment are particularly arranged and configured to face each other and so that the mounting mechanism or sled member 140 can be readily secured to the retractor 102 by engaging the front edge surface (120a, 120b or 120c) and the associated step surface (122a, 122b or 122c) on each of the first and second arms, 112 and 116, and the rack segment 114.

As also shown in the top views of the preferred form of the present invention, the front edge surfaces 120a and 120c of the first and second arm segments that are adjacent to the step surfaces 122a and 122c are of a preferably slightly concave orientation such that the mid point of the first and second arms are spaced apart from each other a greater distance than the distance of either or both of the inner or outer ends of the first and second arms, 112 and 116. Additionally, the outer edge surfaces 121a and 121c of each arm preferably has a greater curvature than the front edge surfaces 120a and 120c of the same arm so that as the retractor 102 spreads the chest of the patient, the motion of separating the first and second arms, 112 and 116, is emphasized to increase the amount the chest of the patient is spread. Therefore, at a given distance of separation between the first and second arms, 112 and 116, the midpoints of the outer surface of the arms will be separated a further distance than at the ends adjacent to the rack segment or at the ends furthest from the rack segment 114 due to the overall generally clam shell shaped configuration of the preferred form of the present invention. An advantage of this configuration is that the surgeon is provided with an opening in the sternum of the patient that is wider in the center than along the edges so that the most common area of work for the surgeon is larger than a conventional retractor for the same amount of separation.

Additionally, the top surface of each of the arms, 112 and 116, preferably include a plurality of slots 123 extending generally perpendicular to the lengthwise dimension of each arm. These slots 123 extend from the front edge surfaces 120a and 120c; through the step surfaces 122a and 122c; and to the outer edge surfaces 121a and 121c, respectively on each of the first and second arms, 112 and 116. These slots 123 are configured to extend through the front edge surface 120a and 120c of each arm, 112 and 116, to allow the sled member 140 to be moved therealong while not cutting or interfering with any sutures that may be positioned in the slots. Additionally, each of the slots 123 preferably include a through hole 124 in communication with the slot and extending through the arm. In the preferred use of the present invention, the slots 123 may be used to position sutures that have been threaded through the pericardium of the patient therein so that the pericardium or other tissue is retracted and held out of the line of sight of the surgeon by the sutures to better expose the desired surface of the heart. With the preferred form of the present invention, the sutures and clamps are retained out of the working area of the surgeon. The portion of the through hole 124 adjacent to the top and bottom surfaces of the arm are preferably tapered so that distal end of the clamps or other instruments that are used to hold the sutures may be placed and retained therein during the procedure. By allowing the distal ends of the instruments to be placed into the through holes 124, the sutures are held in a secure low profile position during the procedure and may be adjusted as needed at any time by lifting the instrument and then releasing the clamp and pulling the suture through the clamp and subsequently closing the clamp while it remains in the through hole or replaced therein. Additionally, it is anticipated that some surgeons may use these through holes to suture the retractor to the patient to minimize possible extraneous movement of the retractor during the procedure.

In an exemplary embodiment of the present invention, the bottom surface of each of the first and second arms, 112 and 116, on the retractor 102 include removable sternal blades 130 attached thereto. Each blade 130 is removable so as to facilitate the use of the retractor in a full or mini-sternotomy procedure by allowing for the selective positioning and spacing of the blades 130 as desired for the particular procedure as well as for the convenient resterilization of the retractor 102 and blades 130.

As illustrated, the blades 130 are positioned along the bottom surface of the arms 112 and 116 and are preferably pivotal in the horizontal and vertical directions with respect to the arms. The blades 130 are slidable into elongate ridged slots 132 on the bottom surface of the first and second arms, 112 and 116. The blades 130 may swivel a limited distance and are selectively positioned in the slots 132 so as to evenly distribute the retraction forces or pressure along the contour of the sternum of the patient. An upper section 134 of each blade 130 is particularly configured to facilitate the insertion of the blades into the retractor. In particular, the upper section 134 of the blade 130 is configured so that an upward extending and generally oblong shaped lip member is received in the ridged slots 132 located on the bottom surface of the first and second arms, 112 and 116. This surface further includes a raised ball member which slides in a further slot 139 located in the ridged slots. The ball member is slightly depressible so that it may be slid beyond the further slot 139 so that during the initial placement of the retractor, the blades may be positioned to extend nearly linearly along each arm in an insertion position. As the arms are retracted, the inner and outermost blades move to a retraction position to assume a slightly curved shape. In the preferred form of the present invention, the retraction position generally approximates the anatomy of the patient and allows the pressure of the sternum of the patient to be evenly distributed among the blades. The use of the ball member and the further slots and the ridged slots allow the blades to temporarily assume the linear configuration and also rise slightly with respect to the retractor to provide a lower profile and maintain the retraction edge. Once the blades are inserted into the sternum, the slight release of the pressure following the insertion allows the ball member to return to the innermost end of the further slot and the blades may pivot slightly in the vertical and horizontal directions so that the blades follow the slightly curved shape of the retractor to provide optimum leverage to retract the sternum of the patient. The upper section 134 of the blade 130 extends generally along the bottom surface of the first and second arms, 112 and 116 and is positioned so the blade 130 extends a short distance inwardly of the front edge surfaces 120*a* and 120*c* of the arms 112 and 116. The blades 130 also include a lower section 138 which extends downwardly from the upper section 134 of the blade 130 in a curved manner to extend beneath the bottom surface of the retractor to readily engage the sternum of the patient. The lower section also preferably curves backward a short distance towards the outer edge surface 121 of the first and second arms, 112 and 116, to form a blade 130 having an overall C or L shape that facilitates the positioning and retention of the sternum of the patient adjacent thereto. Therefore, the blades 130 in conjunction with the displacement of the first and second arms result in the desired retraction of the tissue, bone etc. for the surgical procedure.

The stabilization arm 104 of the preferred embodiment also includes a sled member 140 operatively connected thereto. The sled member 140 is configured so the surgeon has multiple axis positioning capability for the stabilization device 106 while requiring a minimum of manipulation. The sled member allows movement along a horizontal axis and movement along a vertical axis in response to rotation of the movable knob assembly 188 as described more fully above. In an exemplary embodiment, the bottom section of the sled member 140 includes a front edge lip 142, a movable second lip 143 and an actuator lever 144. The actuator lever 144 is pivotally connected to an elongate slot in the second lip 143 by a pin 145 which is preferably offset with respect to the axis of rotation of the actuator lever 144 so that movement of the actuator lever 144 causes the second lip 143 to move towards and away from the front edge lip 142. The front edge lip 142 is configured so that the interior of this lip conforms generally to the shape and configuration of any of the front edge surfaces 120*a–c* of the retractor. The front edge lip 142 also includes a portion that extends backwards under the front edge surfaces 120*a–c* of the arms and/or rack segment of the retractor so the front edge lip 142 preferably forms an acutely angled surface that is easily secured at any location on any of the front edge surfaces 120*a*, 120*b* or 120*c* of the retractor 102.

As also shown in the drawings, the second lip 143 of the sled member 140 is a semicircular or oblong shaped member that is disposed in the bottom of the sled member 140 a distance back from the front edge lip to selectively engage the recessed side of any of the step surfaces 122*a–c* of the retractor. The second lip 143 also is generally configured so the inside interior surface of the sled member 140 extends arcuately across and lies upon the top surface of the retractor 102 between a front edge surface 120*a–c* and the associated step surface 122*a–c* of the retractor. The second lip 143 is slidably mounted on the bottom side of the sled member 140 and is movable in response to rotation of the actuator lever 144 to form an acute step surface engaging angle between the sled second lip 143 and the inside interior surface to securely retain the selected step surface 120*a*, 120*b* or 120*c* therein.

In the preferred embodiment of the present invention, the sled member 140 also includes another section including a ball or knob member 160 thereon. This portion of the sled member 140 provides the surgeon with the rotational movement of the stabilization arm 104 in a combination of horizontal and vertical directions, all of which are advantageously controlled by the operation of the movable knob assembly 188 that is spaced apart therefrom. Furthermore, the arm segment 180 may be oriented such that the angle formed between the first shaft segment 182 and the second shaft segment 186 is up, down or sideways and at an acute or obtuse angle. The movable knob assembly 188 may be positioned above or below the ball member 160 on the sled member 140 to provide the surgeon with further options to minimize the interference of the stabilization arm with access to the surgical site and to increase or decrease the effective length and orientation of the stabilization arm 104.

The ball member 160 of the preferred embodiment extends generally linearly or parallel to the lengthwise dimension of the sled member 140. Alternately, as shown in FIG. 9, the ball member 160 may be oriented to extend upwardly from the portion of the bottom section of the sled member 140 to form a first or vertical axis of rotation between the bottom section that includes the front edge lip 142, second lip 143 and the actuator lever 144 described above and the second shaft segment 186 described above. These arrangements enable the proximal connector 162 of the second shaft segment 186 to be fully rotatable with respect to the sled member 140 independently of whether or not the sled member is locked into position along the arms and/or rack segment of the retractor. Additionally, this orientation allows the sled member to be preferably positioned inwardly or directly above the front edge of the retractor as shown. This orientation significantly increases the range of motion of the sled member and therefore the range of motion of the stabilization arm and, ultimately, significantly increases the versatility and range of motion of the stabilization device. For example, movement of the sled member 140 and rotation of the stabilization arm 104 will allow the user to position the stabilization device 106 beneath the arms and/or rack segment by allowing the angle between the first shaft segment 182 and second shaft segment 186 to be acute so the stabilization device extends inwardly of the front edge 120 of the retractor 102.

These features are additionally enhanced by the use of the first and second shaft segments in combination with the movable knob assembly 188 that is spaced apart from the sled member 140. These features allow the user to position the stabilization device in a wide variety of positions including under the arms of the retractor while ensuring that the proximal portion of the arm segment is only minimally positioned in or upstanding from the surgical field. This ability to select a wide variety of orientations is particularly useful in situations where the posterior surface of the heart is being operated on as well as in certain situations where the selected portion of the heart is manipulated to a side of the operative field. Additionally, with the first and second shaft segments, 182 and 186, as well as using one or more of these segments having a curvature, the radius of curvature and the angle formed by the first and second shaft segments may be oriented upwardly or downwardly to provide the user with yet another option to locate the optimum position of the stabilization device. For example, when the arm segment is oriented so the angle formed by the first and second shaft segments faces downwardly, the distal end of the arm segment assumes a low profile to ensure that the arm segment does not interfere with the operation. This is particularly true when the movable knob assembly 188 is oriented above or parallel to the horizontal axis of the retractor arm or rack segment. Similarly, when the angle formed by the first and second shaft segments faces upwardly, the surgeon may approach the surgical field at a sharper angle than with other stabilization systems and this orientation may be further emphasized by orienting the movable knob assembly 188 below the horizontal axis of the arm or rack segment of the retractor. Furthermore, the ball member 160 may also be angled to extend inwardly relative to the retractor to cause the upper section of the sled member and proximal connector 162 of the second shaft segment 186 to extend inwardly of the front edges of the arms and rack segment to further increase the versatility of the present invention. This type of orientation may require the arm segment to be oriented at an angle that is generally greater than perpendicular to the width dimension of the arms or rack segment. In this way, the proximal connector 162 of the second shaft segment 186 is movable about the ball member 160 of the sled member 140 to facilitate the horizontal and rotational positioning of the stabilization arm 104 and stabilization device 106 at the desired predetermined area on the heart of the patient.

Figure 10:
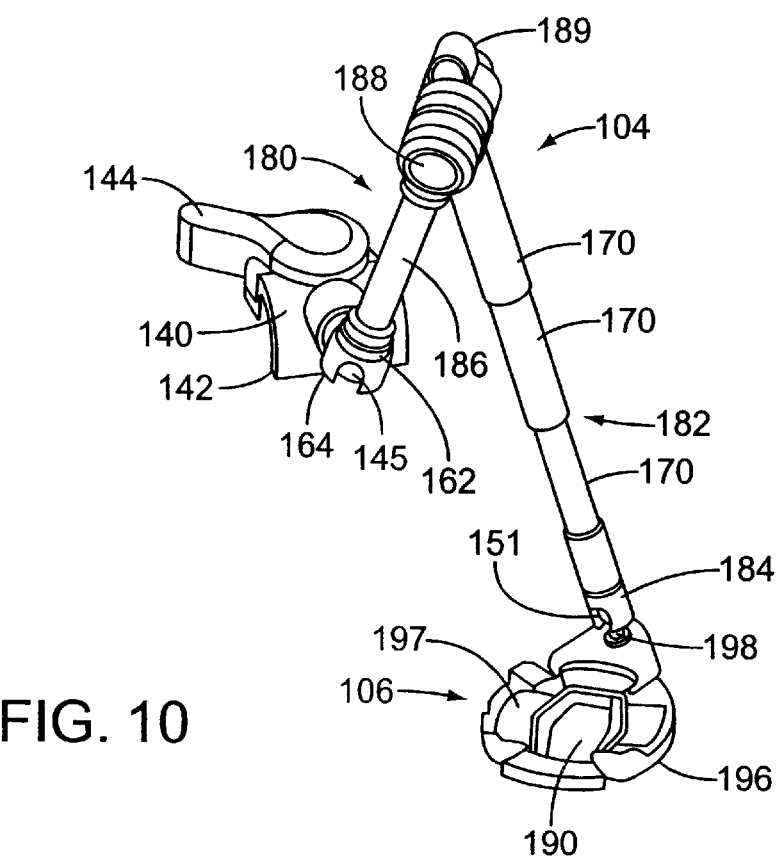
FIG. 10 is a perspective view of an alternate view of the stabilization arm system of the present invention wherein the arm includes telescoping cylinders.

FIG. 10 is illustrative of an alternate form of the present invention wherein the first shaft segment 182 is formed of a plurality of telescoping members 170. In this embodiment, the width of the telescoping members increases proximally from the distal connector 184. These complementary telescoping members may be manually adjustable into a locking position by rotating the telescoping members approximately ¼ turn relative to each other. Alternately, the telescoping members may be locked upon actuation of the movable knob assembly 188 to cause a rod-like member to engage the telescoping members 170 or to cause the locking of the telescoping members in response to a cable or hydraulic pressures. In this embodiment, a further advantage of the present invention is illustrated by providing an adjustable length for the first shaft segment so that this length may be adjusted as needed based on the desired location for the stabilization device or the type of surgical procedure to be performed. Similarly, during set up, the first shaft segment may be adjusted so as to not interfere with the preparation of the surgical site and then the movable knob assembly 188 may be actuated to remotely move the distal connector and stabilization device into the desired location in the surgical site.

The use of the stabilization system 100 according to the preferred aspect of the present invention can be best understood from the following discussion with reference to the drawings. Although the following discussion makes reference to the use of the stabilization system specifically in connection with a coronary artery bypass grafting surgical procedure, the use of the stabilization system of the present invention is not limited to such uses.

After appropriately preparing and positioning the patient for the surgical procedure and completing those actions required in advance of the use of the stabilization system, the arms 112 and 116 of the retractor 102 would be closed such that the upper portion 134 of the blades 130 are generally abutting each other. The surgeon then positions the lower sections 138 of each of the blades adjacent to the incision and pushes down on the retractor or otherwise manipulates the blades and the patient so the blades are pushed through the incision and past the sternum.

After inserting the retractor, the surgeon displaces the two retractor arm segments 112,116 with respect to each other by rotating the handle 118 on the second arm segment 116. As the surgeon opens the sternum of the patient, they also release any underlying connective tissue and open the pericardium surrounding the heart of the patient. In order to provide for visualization of the heart, the pericardium that surrounds the heart is retracted by placing sutures (not shown) through the pericardium and then threading the sutures through the slots 123 on the retractor arms to ensure that the sutures are spaced apart from the operative field. As mentioned above, the clamps (not shown) holding the sutures may then be positioned in the slots so that the distal end of the clamping instrument is positioned in the through holes 124 or a suture organizer may be used. This allows the sutures and clamps to be positioned out of the way of the surgeon for the subsequent procedure. After performing any subsequent actions to further open the sternum of the patient to create the desired field of view and assess the viability of the heart to perform the bypass grafting procedure on one or more vessels, the surgeon mounts the stabilization arm 104 onto one of the retractor arm segments 112,116 or the rack segment 114 in the position that they anticipate will provide the best access while minimizing the obstruction of their view for the particular procedure.

It should be recognized that the bypass grafting procedure may involve the arteries or branches thereof on nearly any surface of the heart including the posterior or backside of the heart. Therefore, having the capability to mount the stabilization arm to the rack segment 114 or either of the arms, 112 or 116, of the retractor can be particularly advantageous. With the preferred form of the present invention, the stabilization arm 104 may also be positioned with the arc formed by the relative orientation of the first shaft segment 182 and the second shaft segment 186 to each other such that the stabilization arm 104 is be positioned above or below the longitudinal axis of the ball member 160 and/or the horizontal axis of the retractor member. The retractor 102 is typically arranged on the body so the throat of the retractor faces the head of the patient and the surgeon is typically located on one side of the patient while a nurse is located on the other side of the patient and instruments are passed across the body of the patient throughout the procedure. Therefore, with the preferred form of the present invention, the surgeon has an additional surface to choose from when they are deciding which surface will provide the best access to the desired surface of the heart while not interfering with the procedure.

To mount the stabilization arm 104 onto the retractor 102, the surgeon rotates the sled actuator lever 144 so the second lip 143 is in a disengaged position and is spaced from the front edge lip 142 of the sled member 140. After so configuring the sled member 140, the surgeon positions the sled member 140 on the retractor 102 at any of a number of available positions on the arms, 112 and 116, or the rack segment 114 by positioning the front edge lip 142 over the front edge of the selected arm or rack segment. With the preferred configuration of the sled member 140, the surgeon need not slide the sled member along the entire length of a retractor arm or be required to select from a limited number of predetermined positions, but can place the sled member 140 directly at the desired position. In this way, a surgeon can removably position the sled member 140 anywhere on the rack segment 114 or the arms 112, 116 of the retractor 102 without having to first assemble the retractor with a sled member 140 initially positioned in any of these predefined areas. An advantage of this configuration is that the surgeon may initially position the sled member 140 in a position that they anticipate will be close to where they will ultimately want it. If during the procedure, a different location is needed or provides better access, the surgeon may either slide the sled member 140 along the previously selected arm or rack segment to the desired location or they may remove the sled member 140 from the retractor and try various locations to see which location on the arms and rack segment provides the best access for the particular procedure. In addition, such a sled configuration also allows the surgeon to perform certain surgical procedures without having to worry about the sled member 140 cutting or interfering with any sutures that may be passing over the retractor while positioning the sled member 140. Furthermore, if multiple blood vessels are operated on or access to multiple surfaces is desired, the orientation of the sled member may be readily adjusted to accommodate the needs of the particular part of the procedure.

The surgeon may next fix the sled member in place by positioning the front edge lip 150 of the sled member 140 over the front edge surface 120*a*, 120*b* or 120*c* on the desired area of the retractor 102 and then rotating the sled actuator lever 154 partially or fully, as desired, so the second lip 143 contacts and engages the vertical extending surface of the corresponding step surface 122*a–c* on the retractor 102. Once the surgeon has placed the sled member on the retractor in the approximate desired location along the arm or rack segment of the retractor, they may then initially position the stabilization device 106 near the ultimate desired location along the surface of the heart by loosening the movable knob assembly 188 and rotating the knob 189 to loosen the connection between the proximal connector 162 and the sled member 140 and orient the stabilization device 106 in the tentative desired position. It should be recognized that this process may include orienting the arc formed between the first shaft segment 182 and the second shaft segment 186 of the arm segment 180 up, down or linearly and may be repeated as often and whenever necessary to modify the position of the stabilization device 106 at the desired location or area of the heart.

Thereafter, the surgeon may rotate the proximal connector 162 about the ball member 160 of the sled member 140 and also move the arm segment 180 lengthwise and/or rotationally with respect to the sled member 140 so as to position the stabilization device 106 with respect to the predetermined area of the heart to be stabilized. Once the surgeon is satisfied with the location of the stabilization device 106 on the heart of the patient, the surgeon may tighten the knob 189 of the movable knob assembly 188 to ensure that the stabilization arm 104 and stabilization device 106 are retained in the desired position throughout the remainder of the procedure. Once the stabilization device 106 is in the desired contacting relationship with the predetermined area of the heart, the surgeon may tighten the knob 189 of the stabilization arm 104 so as to prevent further rotation and movement of the proximal connector 162 of the arm segment relative to the sled member and to prevent further movement of the stabilization device 106 relative to the distal connector 184. The surgeon may also gradually tighten the knob 189 of the arm segment 180 so as to tighten the connection between the distal connector 184 on the arm segment and the post member 196 on the stabilization device 106 to allow fine adjustment of the stabilization device and then ultimately to prevent further motion of the stabilization device 106 about the end of the stabilization arm 104. Finally, the actuator lever 144 may be rotated to a final locked position to prevent sliding of the sled member relative to the retractor. It is anticipated that a preferred form of the present invention provides that the movable knob assembly 188 of the arm segment 180 may be arranged so that the connection between the distal connector 184 on the first shaft segment 182 and the post member 196 of the stabilization 106 is initially tightened during the initial rotation of the knob 189. Further rotation of the knob 189 will then tighten the connection between the proximal connector 162 of the second shaft segment 186 and the ball member 160 of the sled member. Thereafter, continued rotation of the knob 189 will prevent any further relative movement so that the stabilization arm system will retain the stabilization device relative to the retractor.

After completing the grafting procedure, the surgeon may then remove the stabilization arm 104 and stabilization device 106 by essentially reversing the above described steps or the surgeon may simply release the actuator lever 144 and remove the entire stabilization arm and stabilization device from the operative field. Similarly, the actuator lever may be moved to a position between the engaged and disengaged positions so that the stabilization arm may be moved out of the way while a subsequent procedure is performed or to attach a new stabilization device thereon.

In the foregoing discussion, the stabilization system of the present invention is described in terms of clamping and supporting a stabilization device. It is within the scope of the present invention, however, for the system to be configured to removably secure any of a number of surgical instruments to the retractor or similar device such as for example diaphragm or valve retractors. Additionally, although one stabilization arm is described as being in use at a time, it is within the scope of the present invention for plurality or a multiplicity of stabilization arms to be secured to the retractor. For example, one stabilization arm could be provided to support a diaphragm retractor and another stabilization arm provided to support a tissue stabilizer or suction device.

Although a preferred embodiment of the invention has been described using specific terms, such description is for illustrative purposes only, and it is to be understood that changes and variations may be made without departing from the spirit or scope of the following claims.

What is claimed is:

1. A system for use in surgical procedure on a human patient, comprising:

a retractor having a plurality of retractor arms thereon and a segment interconnecting said retractor arms wherein said retractor arms are movable with respect to each other;

a stabilization arm operatively positionable with respect to said retractor and said stabilization arm being sized to hold a medical device in a desired position during a medical procedure;

a stabilization device operatively positioned on said stabilization arm;

a connector which is selectively mountable on said retractor and pivotal with respect to said stabibzation arm; and a knob assembly associated with the stabilization arm wherein the knob assembly is spaced apart from the retractor and stabilization device and is adjustable to control the positioning of the stabilization device relative to the stabilization arm and wherein the knob assembly is attached to adjacent end portions of a pair of shaft segments to interconnect the shaft segments and allow the relative movement thereof.

2. The system of claim 1 wherein said knob assembly is adjustable to control the positioning of the stabilization arm relative to the retractor and stabilization device.

3. The system of claim 1 wherein said stabilization arm includes a a distal shaft segment and a proximal shaft segment wherein the shaft segments are movable with respect to each other.

4. The system of claim 1 wherein said stabilization arm includes a distal end portion on a distal shaft segment and a proximal end portion on a proximal shaft segment wherein said distal end portion includes said stabilization device removably mounted thereon and the knob assembly is attached to the opposite end thereof.

5. The system of claim 4 wherein said stabilization arm includes a plurality of connectors thereon and said connectors are movable in response to the movement of knob assembly member.

6. The system of claim 4 wherein said stabilization arm includes the knob assembly member thereon and actuation of said knob member affects the movement of said stabilization device on said distal end portion of said distal shaft segment.

7. The system of claim 1 wherein movement of said knob assembly causes the distal and proximal movement of a first rod member through at least one of the shaft segments and said first rod member selectively engages a portion of said stabilization device in one of the distal and proximal movements thereof.

8. The system of claim 7 wherein said rod member thereon is movable between engaged and disengaged positions to engage and disengage said stabilization device from said stabilization arm.

9. The system of claim 7 wherein said rod member extends into a slot member located on a distal end portion of one of the shaft segments in the engaged position and is space apart therefrom in the disengaged position.

10. The system of claim 1 wherein movement of said knob assembly causes the distal and proximal movement of a second rod member and said second rod member selectively passes through a portion of the stabilization arm between engaged and disengaged positions.

11. A system for use in a surgical procedure, comprising:
a retractor having a plurality of retractor arms thereon and a segment interconnecting said retractor arms wherein said retractor arms include an edge surface and are movable with respect to each other;
a stabilization arm having distal and proximal end portions on distal and proximal shaft segments and said stabilization arm is operatively positionable with respect to said retractor and sized to hold a medical device in a desired position during a medical procedure;
a connector which is attachable to said retractor and which interacts with said stabilization arm to position said distal end portion of said distal shaft segment of the stabilization arm and said medical device in a desired position relative to the retractor; and
a control assembly associated with said stabilization arm and adjacent to the distal end portion of said proximal shaft segment and said proximal end portion of said distal shaft segment of said stabilization arm wherein said control assembly is movable between first and second positions and wherein the position of the stabilization arm relative to the retractor is adjustable in a first position and is fixed in a second position thereof.

12. The system of claim 11 wherein said stabilization arm includes a a distal shaft segment and a proximal shaft segment wherein the shaft segments are movable with respect to each other.

13. The system of claim 11 wherein said distal end portion of said stabilization arm is rotatable with respect to said proximal end of said stabilization arm.

14. The system of claim 11 wherein said stabilization arm includes a removable medical device on the distal end portion thereof.

15. The system of claim 14 wherein actuation of said control assembly on said stabilization arm affects the movement of said medical device on said distal end portion of said stabilization arm.

16. The system of claim 11 wherein actuation of a member on said control assembly of said stabilization arm causes the longitudinal movement of a movable member associated with said stabilization arm to restrict the movement of said medical device relative to said distal end portion of said stabilization arm.

17. The system of claim 16 wherein said stabilization arm includes a plurality of movable members thereon that are movable between a first position wherein the stabilization arm is fixed relative to the medical device and a second position wherein the stabilization arm is movable relative to the medical device.

18. The system of claim 11 wherein said stabilization arm includes a tubular portion having a movable member therein.

19. The system of claim 18 wherein said movable member moves between engaged and disengaged positions relative to said medical device.

20. A stabilization system for use in a surgical procedure, comprising:
a stabilization arm having a control assembly and distal and proximal end portions thereon and having a plurality of shaft segments and said stabilization arm being operatively positionable with respect to a patient to hold a stabilization device in a desired position during a medical procedure and wherein the control assembly is spaced apart from the distal and proximal end portions of said stabilization arm; and
said stabilization device operatively connected to said distal end portion of said stabilization arm and including a surface thereon which is sized to stabilize a portion of the tissue of a patient during a medical procedure and wherein movement of said stabilization device relative to said stabilization arm is in response to actuation of the control assembly on said stabilization arm.

21. The system of claim 20 wherein said stabilization arm includes a plurality of tubular members extending between said distal and proximal end portions thereof and at least one movable member therein to translate movement of the control assembly into movement of a member on said distal end portion of said stabilization arm.

22. The system of claim 21 wherein said at least one movable member is movable distally and proximally in at least one of said plurality of said tubular members of said stabilization arm.

23. The system of claim 22 wherein said stabilization arm includes a further movable member extending between said control assembly and said proximal end portion of said stabilization arm.

24. The system of claim 20 wherein said stabilization arm includes elongate distal and proximal shaft segments and said control assembly is positioned therebetween.

25. The system of claim 24 wherein said distal and proximal shaft segments include movable members therein and at least one of said movable members is movable between a first position wherein the stabilization device is movable relative to the stabilization arm and a second position wherein the stabilization device is fixed relative to the stabilization arm.

26. A stabilization system for use in a surgical procedure, comprising:
- a stabilization arm having distal and proximal end portions and first and second shaft segments and a control assembly associated therewith and further including said distal end portion arranged hold a stabilization device in a desired position during a medical procedure and wherein said proximal end portion is arranged to engage a member on a retractor and wherein the stabilization arm includes at least one movable member therein to translate movement of the control assembly outwardly therefrom, through the first and second shaft segments and to the distal and proximal end portions thereof; and
- a sled member having horizontal and vertical axes of rotation and a member thereon for engaging the proximal end portion of the stabilization arm and wherein said proximal end portion is movable to a fixed position relative to said member in response to movement of said control assembly which is spaced apart therefrom.

27. The system of claim 26 wherein said stabilization arm includes a distal connector thereon and said distal connector is movable with respect to said control assembly in a first position of said control assembly and is in a fixed position relative thereto in a second position of said control assembly.

28. The system of claim 26 further including a retractor wherein the sled member is connectable thereto and the sled member includes an actuation member thereon that is movable between first and second positions and the stabilization arm is movable relative to the sled member in the first and second positions of the actuation member and the sled member is movable relative to the retractor in the first and second positions of the control assembly.

29. A method of performing a surgical procedure, comprising:
- providing a stabilization arm having a control assembly and distal and proximal end portions thereon and having a plurality of shaft segments and wherein the stabilization arm is operatively positionable with respect to a patient to hold a stabilization device in a desired position during a medical procedure;
- providing the control assembly in an orientation along the stabilization arm such that the control assembly is spaced apart from the distal and proximal end portions of said stabilization arm wherein;
- providing a stabilization device which is operatively connected to said distal end portion of said stabilization arm and including a surface thereon which is sized to stabilize a portion of the tissue of a patient during a medical procedure and wherein said stabilization device is movable with respect to said stabilization arm in response to actuation of the control assembly on said stabilization arm; and
- moving the control assembly between first and second positions wherein the stabilization device is movable relative to the distal end portion of the stabilization arm in the first position and is rigidly retained relative to the stabilization arm in the second position thereof.

30. The method of claim 29 wherein the proximal end portion of the stabilization arm is movable relative to a sled member in the first position and rigidly retained relative thereto in the second position and wherein the method includes the step of positioning the stabilization device and stabilization arm in a desired position relative to the tissue of a patient in the first position of the control assembly and rigidly retaining the stabilization arm and stabilization device in the desired position when the control assembly is moved to the second position.

31. The method of claim 29 wherein a surgical retractor is provided and the stabilization arm is attachable thereto via a sled member and wherein the sled member includes an actuation lever thereon that is movable between first and second positions and the sled member is movable along the retractor in the first position thereof and is fixedly retained thereon in the second position thereof.

32. The method of claim 31 wherein the stabilization arm is movable relative to the sled member in the first and second positions of the actuation lever and the sled member is movable relative to the retractor in the first and second positions of the control assembly.

* * * * *